United States Patent [19]

Nakata et al.

[11] Patent Number: 4,615,348

[45] Date of Patent: Oct. 7, 1986

[54] METHOD FOR ADHERING ARTIFICIAL NAIL

[75] Inventors: Chiaki Nakata; Toshio Takenaka, both of Osaka, Japan

[73] Assignees: Taoka Chemical Company Limited; Sumitomo Chemical Co. Limited, both of Osaka, Japan

[21] Appl. No.: 449,191

[22] Filed: Dec. 13, 1982

[30] Foreign Application Priority Data

Dec. 11, 1981 [JP] Japan .................................. 56-199844
Dec. 14, 1981 [JP] Japan .................................. 56-201091

[51] Int. Cl.$^4$ ...................... A61K 7/00; A61K 7/104; A45D 31/00
[52] U.S. Cl. ......................................... 132/73; 424/61
[58] Field of Search .................. 132/73, 88.5; 156/60, 156/61; 424/61, 81

[56] References Cited

U.S. PATENT DOCUMENTS 4,007,748 2/1977 Matranga et al. .................... 132/73
4,171,416 10/1979 Motegi et al. ......................... 424/61
4,407,310 10/1983 Jadow ................................... 132/73

*Primary Examiner*—Richard J. Apley
*Assistant Examiner*—Gregory Beaucage
*Attorney, Agent, or Firm*—Wegner & Bretschneider

[57] ABSTRACT

A method for adhering an artificial nail to a natural nail by the use of an adhesive comprising at least one of α-cyanoacrylates of the formula:

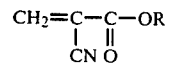

wherein R is n-propyl, isopropyl, n-butyl, isobutyl, methoxyethyl, ethoxyethyl or etrahydrofurfuryl. This method does not generate heat and assures easy removal of the adhesion with a conventional solvent.

7 Claims, No Drawings

METHOD FOR ADHERING ARTIFICIAL NAIL

BACKGROUND OF THE INVENTION

1. Field of the Invention

The present invention relates to a method for adhering an artificial nail onto a natural nail. More particularly, it relates to a method for adhering an artificial nail onto a natural nail by the use of an adhesive comprising a certain specific α-cyanoacrylate.

2. Description of the Prior Art

α-Cyanoacrylates such as methyl α-cyanoacrylate and ethyl α-cyanoacrylate are easily anionically polymerized and cured within a short period of time by moisture on a solid surface or in the air or by anionic active species (e.g. alkaline substances) in the absence of any catalyst and without heating. Accordingly, they are widely used as so-called instant adhesives to adhere rubbers, plasics, metals, glass, etc. and employed in various industries (e.g. automobile industry, light electrical appliances industry, woodworks). Recently, they have been also used in the fields of medicine and cosmetics, for example, in repairing nails or fitting artificial nails onto natural nails.

Nails protect tips of fingers by nature and also ornament women's fingers. In order to decorate natural nails, manicure and/or artificial nails are applied to them. A conventional method for fitting an artificial nail, made of an elastic plastic sheet in most cases, onto a natural nail comprises adhering the artificial nail to the whole surface or tip of the natural nail with an α-cyanoacrylate adhesive, trimming the artificial nail and finishing it with manicure.

Since, however, the surface of a natural nail has a temperture close to that of a body and has a certain amount of moisture, an α-cyanoacrylate as conventionally employed for adhesion such as methyl α-cyanoacrylate and ethyl α-cyanoacrylate starts to polymerize rapidly, with generation of heat. In order to remove an artificial nail once adhered to a natural nail with such adhesive, an organic solvent such as acetone is used. The adhesivity of such an adhesive is strong, and therefore the solvent must be used repeatedly, whereby some lines are produced on the surface of the natural nail and the gloss or smoothness of the natural nail is lost.

SUMMARY OF THE INVENTION

As a result of the extensive study to solve the problems present in the conventional adhesive, it has now been found that certain specific α-cyanoacrylates are effective in adhering an artificial nail to a natural nail wihtout such problems.

According to the present invention, there is provided an adhesive for adhering an artificial nail to a natural nail, comprising at least one α-cyanoacrylate of the formula:

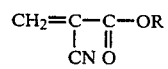 (I)

wherein R is n-propyl, isopropyl, n-butyl, isobutyl, methoxyethyl, ethoxyethyl or tetrahydrofurfuryl. Among the α-cyanoacrylates (I), the methoxyethyl, ethoxyethyl and tetrahydrofurfuryl esters are particularly advantageous in having no irritant odor. Also, their use makes possible the incorporation of perfume to enhance the commercial value of the adhesive.

DETAILED DESCRIPTION OF THE INVENTION

The essesntial component in the adhesive of the invention is the α-cyanoacrylate (I). Thus, the adhesive comprises at least one of the α-cyanoacrylates (I) in an amount of 1 to 100% by weight, preferably 3 to 100% by weight. In addition, the adhesive may include methyl α-cyanoacrylate and/or ethyl α-cyanoacrylate as a second component. The weight ratio of the second component to the α-cyanoacrylate (I) is usually not greater than 100:1, preferably not greater than 100:3. When the content of the α-cyanoacrylate (I) is lower than the lower limit, the problems associated with the conventional α-cyanoacrylate will be produced.

The adhesive of the invention may further contain stabilizing agents (e.g. sulfur dioxide, p-toluenesulfonic acid, propionic acid, hydroquinone, monomethoxyhydroquinone), thickening agents (e.g. polymethyl methacrylate, polyvinyl acetate), plasticizers (e.g. dioctyl phthalate, dibutyl phthalate), solvents (e.g. ethyl acetate, butyl acetate), perfumes and dyes, etc. in appropriate amounts.

The present invention will be hereinafter explained in detail by the following Examples, wherein part(s) are by weight unless otherwise indicated.

EXAMPLES 1 TO 13 AND COMPARATIVE EXAMPLES 1 AND 2

To the α-cyanoacrylate (I) as shown in Table 1, there were added sulfur dioxide (20 ppm) and hydroquinone (500 ppm) to prepare an α-cyanoacrylate adhesive for artificial nails. The heat of polymerization was measured by exposing a thermometer to the atmosphere of ammonia vapor at a temperature of 20° C. and a relative humidity of 55 to 60% for 5 minutes, dropping two drops of the adhesive on the detector of the thermometer, reading the elevated temperature and recording the maximum temperature. The results are shown in Table 1.

With the adhesive, two pieces of artificial nails ("5 Second Tiger Nails" manufactured by Viam Corp. (USA)) were adhered to each other. After 24 hours, the adhered artificial nails were immersed in a remover liquid ("Super Glur Remover" manufactured by Super Glue Corp. (USA)), and the time necessary to separate the artificial nails was measured. The results are shown in Table 1.

The artificial nails as used above were adhered to the natural nails of 20 women. Then, the artificial nails were removed from the natural nails with the remover liquid as used above. These procedures were repeated 10 times. With the methyl α-cyanoacrylate adhesive, 3 nails of 2 women lost gloss, and 1 nail was slightly scratched. With the ethyl α-cyanoacrylate adhesive, 1 nail was damaged. On the other hand, no damage was found with the adhesives of Examples 1 to 13.

TABLE 1

| α-cyanoacrylate (I) | Maximum temperature (°C.) | Time necessary to remove nails (min) |
| --- | --- | --- |
| Example | | |
| 1 n-Propyl α-cyanoacrylate | 44 | 5 |
| 2 Isopropyl α-cyanoacrylate*1 | 30 | 4 |

TABLE 1-continued

| | α-cyanoacrylate (I) | Maximum temperature (°C.) | Time necessary to remove nails (min) |
|---|---|---|---|
| 3 | n-Butyl α-cyanoacrylate | 41 | 4 |
| 4 | Isobutyl α-cyanoacrylate | 26 | 3 |
| 5 | Isopropyl α-cyanoacrylate (50%) and ethyl α-cyanoacrylate (50%) | 34 | 4 |
| 6 | Isobutyl α-cyanoacrylate (50%) and ethyl α-cyanoacrylate (50%) | 28 | 4 |
| 7 | Isopropyl α-cyanoacrylate*[2] (8%) and ethyl α-cyanoacrylate (92%) | 42 | 5 |
| 8 | Methoxyethyl α-cyanoacrylate | 37 | 2 |
| 9 | Ethoxyethyl α-cyanoacrylate*[1] | 35 | 2 |
| 10 | Tetrahydrofurfuryl α-cyanoacrylate | 34 | 2 |
| 11 | Ethoxyethyl α-cyanoacrylate (50%) and ethyl α-cyanoacrylate (50%) | 40 | 4 |
| 12 | Ethoxyethyl α-cyanoacrylate*[2] (10%) and ethyl α-cyanoacrylate (90%) | 42 | 4 |
| 13 | Ethoxyethyl α-cyanoacrylate (50%) and n-butyl ethyl α-cyanoacrylate (50%) | 37 | 3 |
| Comparative | | | |
| 1 | Methyl α-cyanoacrylate | 58 | 25 |
| 2 | Ethyl α-cyanoacrylate | 49 | 10 |

Note:
*[1]C.I. Acid Red No. 50 (400 ppm) added to make color pink.
*[2]C.I. Acid Red No. 52 (400 ppm) added to make color pink.

What is claimed is:

1. A method for adhering an artificial nail to a natural nail and later removing the artifical nail which comprises the steps of applying an adhesive, comprising at least one α-cyanoacrylate of the formula:

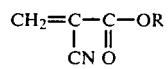

wherein R is n-propyl, isopropyl, n-butyl, isobutyl, methoxyethyl, ethoxyethyl or tetrahydrofurfuryl, to at least one of the artificial nail and the natural nail, contacting the artificial nail with the natural nail, and separating the artificial nail from the natural nail with an adhesive remover, substantially without damage to the natural nail, such that said separation can be easily accomplished in five minutes or less.

2. The method according to claim 1, wherein R in the formula is n-propyl, isopropyl, n-butyl or isobutyl.

3. The method according to claim 1, wherein R in the formula is methoxyethyl, ethoxyethyl or tetrahydrofurfuryl.

4. The method according to claim 1, wherein the adhesive further comprises at least one of methyl α-cyanoacrylate and ethyl α-cyanoacrylate.

5. The method according to claim 1, wherein said α-cyanoacrylate is present in the adhesive in the amount of at least 1 percent by weight.

6. The method according to claim 1, wherein the amount of adhesive is at least 3 percent by weight.

7. The method according to claim 1, further comprising repeating the applying, contacting and separating steps.

* * * * *